US012589382B2

(12) United States Patent
Hur et al.

(10) Patent No.: US 12,589,382 B2
(45) Date of Patent: Mar. 31, 2026

(54) RUTHENIUM OXIDE AND CATALYST COMPRISING SAME

(71) Applicant: SOGANG UNIVERSITY RESEARCH & BUSINESS DEVELOPMENT FOUNDATION, Seoul (KR)

(72) Inventors: Nam Hwi Hur, Seoul (KR); Hee-Jung Yang, Suwon-si (KR)

(73) Assignee: SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 539 days.

(21) Appl. No.: 18/157,093

(22) Filed: Jan. 20, 2023

(65) Prior Publication Data

US 2023/0182118 A1     Jun. 15, 2023

Related U.S. Application Data

(63) Continuation of application No. PCT/KR2021/009240, filed on Jul. 19, 2021.

(30) Foreign Application Priority Data

Jul. 20, 2020    (KR) ........................ 10-2020-0089573
Jun. 23, 2021    (KR) ........................ 10-2021-0081838

(51) Int. Cl.
   *B01J 23/46*        (2006.01)
   *B01J 35/70*        (2024.01)
   (Continued)

(52) U.S. Cl.
   CPC ............. *B01J 23/462* (2013.01); *B01J 35/70* (2024.01); *B01J 37/10* (2013.01); *C01G 55/004* (2013.01);
   (Continued)

(58) Field of Classification Search
   CPC . B01J 23/462; B01J 35/70; B01J 37/10; B01J 2235/15; B01J 2235/00; B01J 37/16; B01J 37/18; C01G 55/004; C01G 55/00; C07C 5/10; C07C 2523/46; C07C 2601/14; C07D 209/86; C01P 2002/72;
   (Continued)

(56) References Cited

U.S. PATENT DOCUMENTS

2017/0064822 A1*  3/2017  Jung ........................ H05K 1/09

FOREIGN PATENT DOCUMENTS

KR     10-2017-0005959 A     1/2017
KR     10-2017-0045669 A     4/2017
   (Continued)

OTHER PUBLICATIONS

International Search Report of PCT/KR2021/009240 dated Oct. 26, 2021.
   (Continued)

*Primary Examiner* — Daniel Berns
*Assistant Examiner* — Joshua Maxwell Speer
(74) *Attorney, Agent, or Firm* — Sughrue Mion, PLLC

(57) ABSTRACT

The present disclosure relates to a novel ruthenium oxide, a method of preparing the same, and a catalyst for selective hydrogenation of an aromatic compound or an unsaturated compound including the ruthenium oxide.

12 Claims, 6 Drawing Sheets

(51) Int. Cl.

| | |
|---|---|
| *B01J 37/10* | (2006.01) |
| *C01G 55/00* | (2006.01) |
| *C07C 5/10* | (2006.01) |
| *C07D 209/86* | (2006.01) |

(52) U.S. Cl.
CPC .............. *C07C 5/10* (2013.01); *C07D 209/86* (2013.01); *B01J 2235/00* (2024.01); *B01J 2235/15* (2024.01); *C01P 2002/72* (2013.01); *C01P 2002/76* (2013.01); *C01P 2002/77* (2013.01); *C01P 2002/85* (2013.01); *C01P 2002/88* (2013.01); *C01P 2002/89* (2013.01); *C07C 2523/46* (2013.01)

(58) Field of Classification Search
CPC .............. C01P 2002/76; C01P 2002/77; C01P 2002/85; C01P 2002/88; C01P 2002/89; C10G 45/40; C10G 45/52
See application file for complete search history.

(56) References Cited

FOREIGN PATENT DOCUMENTS

| | | |
|---|---|---|
| KR | 10-1884928 B1 | 8/2018 |
| KR | 10-2019-0012587 A | 2/2019 |
| KR | 10-2019-0051370 A | 5/2019 |
| WO | 2011016688 A2 | 2/2011 |

OTHER PUBLICATIONS

Julian Haines et al., Phase transitions in ruthenium dioxide up to 40 GPa: Mechanism for the rutile-to-fluorite phase transformation and a model for the high-pressure behavior of stishovite $SiO_2$, Physical Review B, vol. 48, No. 18, Nov. 1, 1993.
Se Yun Kim et al., Facile and Accelerated Production of $RuO_2$ Monolayers via a Dual-Step Intercalation Process, Inorganic Chemistry Frontiers, vol. 7, Feb. 13, 2020, pp. 1445-1450.
Sreedhar Gundekari et al., Hydrous ruthenium oxide: A new generation remarkable catalyst precursor for energy efficient and sustainable production of-valerolactone from levulinic acid in aqueous medium, Applied Catalysis A, General, vol. 569, pp. 117-125.
O. Kosohin et al., Electrochemical Oxidation of Thiocyanate on Metal Oxide Electrodes, Materials Today: Proceedings, vol. 6, pp. 219-226.

* cited by examiner

RUTHENIUM OXIDE AND CATALYST COMPRISING SAME

CROSS-REFERENCE TO RELATED APPLICATIONS

This application is a continuation of PCT Application No. PCT/KR2021/009240, filed on Jul. 19, 2021, which claims priority to Korean Patent Application Nos. 10-2021-0081838, filed on Jun. 23, 2021, and 10-2020-0089573, filed on Jul. 20, 2020, all of which are hereby incorporated by reference in their entirety.

TECHNICAL FIELD

The present disclosure relates to a novel ruthenium oxide, a method of preparing the same and a catalyst including the ruthenium oxide for selective hydrogenation of an aromatic compound or an unsaturated compound.

BACKGROUND

The most widely used and known ruthenium oxide is a black solid having a rutile structure with a chemical formula of RuO2. The rutile structure is tetragonal and is a crystal structure found in many transition metal oxides such as TiO2 or VO2. In general, $RuO_2$ is obtained by high-temperature heat treatment of $RuCl_3$ in an oxidizing atmosphere, or by electroplating in a solution in which $RuCl_3$ is dissolved in water. Meanwhile, $RuO_2 \cdot xH_2O$, which is a hydrous ruthenium oxide, is mainly prepared by an electrochemical method, and the hydrous ruthenium oxide is in an amorphous state without crystallinity and is not easily soluble in water but is convenient to use. For this reason, $RuO_2 \cdot xH_2O$ is widely used for preparing a composite containing ruthenium. It has been investigated that there is no report on the separation and synthesis of $RuO_2$ having a structure other than the rutile structure.

There have been reports that $RuO_2$ with rutile structure can be converted into another crystal structure through structural transition by putting it in a diamond anvil cell and applying an ultra-high pressure. The X-ray diffraction data confirmed that when a pressure of 8 GPa or more is applied to $RuO_2$ with rutile structure, the rutile structure transforms to an orthorhombic structure, and when a pressure of 13 GPa or more is applied, the rutile structure transforms to a cubic fluorite-type structure [J. Haines and J. M. Leger, "Phase transitions in ruthenium dioxide up to 40 GPa: Mechanism for the rutile-to-fluorite phase transformation and a model for the high-pressure behavior of stishovite $SiO_2$", Phys. Rev. B 48, 13344(1993)]. However, there has been no concrete report on the synthesis of solid oxides such as $RuO_2$ with orthorhombic and cubic structures under ultra-high pressure.

$RuO_2$ with rutile structure is widely used as an electrode material called DSA (Dimensionally Stable Anode) in an electrolysis reaction because of its low resistivity, excellent thermal stability and strong acid resistance as a conductive material. Also, it is widely used as a major catalyst material in the Deacon process for producing chlorine from hydrochloric acid, the Fischer-Tropsch process for producing hydrocarbon, and the Haber-Bosch process for producing ammonia.

Meanwhile, ruthenium metal nanoparticles are also widely used as a catalyst for hydrogenation of an aromatic compound called LOHC (Liquid Organic Hydrogen Carrier). For example, a material in which ruthenium metal nanoparticles are supported on alumina is used as a catalyst for producing methylcyclohexane ($C_7H_{14}$) having six hydrogen atoms from a compound having three carbon-carbon double bonds, such as toluene ($C_7H_8$), through hydrogenation. Since the hydrogenation is an exothermic reaction, a lower reaction temperature is preferable. In addition, when the reaction is carried out at a high temperature, the C—C bonds are broken and impurities such as methane are generated. In this case, lowering the reaction temperature is preferable, but when the reaction temperature is lowered, the hydrogenation rate is slowed down. Therefore, a high-activity hydrogenation catalyst that enables rapid hydrogenation even at a low temperature needs to be developed for commercialization of LOHC. Also, it is important to develop a novel ruthenium-based catalyst for efficient hydrogenation of an aromatic or unsaturated compound having carbon-carbon double bonds.

DISCLOSURE OF THE INVENTION

Problems to be Solved by the Invention

The present disclosure relates to a novel ruthenium oxide, a method of preparing the same, and a catalyst including the ruthenium oxide for selective hydrogenation of an aromatic compound or an unsaturated compound.

However, problems to be solved by the present disclosure are not limited to the above-described problems, and although not described herein, other problems to be solved by the present disclosure can be clearly understood by those skilled in the art from the following descriptions.

Means for Solving the Problems

A first aspect of the present disclosure provides a ruthenium oxide with a monoclinic structure and represented by the following Chemical Formula I:

$$H_xRuO_2; \hspace{3cm} \text{[Chemical Formula I]}$$

in Chemical Formula I, $0 < x \leq 4$.

A second aspect of the present disclosure provides a method of preparing a ruthenium oxide, including: hydrothermally treating a tetragonal ruthenium oxide in the presence of at least one of carbon monoxide and carbon dioxide, and water in a pressure reactor to obtain a monoclinic ruthenium oxide.

A third aspect of the present disclosure provides a catalyst including the ruthenium oxide according to the first aspect, and the catalyst is used for selective hydrogenation of an aromatic compound or an unsaturated compound.

Effects of the Invention

According to embodiments of the present disclosure, the ruthenium oxide with a monoclinic structure (the monoclinic ruthenium oxide) can be used as a catalyst for selective hydrogenation even at a low temperature.

According to embodiments of the present disclosure, a hydrogenation catalyst including the monoclinic ruthenium oxide with a chemical formula of $H_xRuO_2$ can be reused.

BRIEF DESCRIPTION OF THE DRAWINGS

FIG. 1A to FIG. 1C show X-ray powder diffraction data of a tetragonal rutile ruthenium oxide (FIG. 1A), a monoclinic ruthenium oxide ($H_xRuO_2$) prepared according to an embodiment of the present disclosure (FIG. 1B), and hydrous $RuO_2$ (FIG. 1C), respectively, and the monoclinic ruthenium oxide ($H_xRuO_2$) shows a characteristic X-ray powder diffraction peak different from that of the tetragonal rutile ruthenium oxide.

FIG. 2 is a thermo-gravimetric analysis (TGA) graph of the monoclinic ruthenium oxide according to an embodiment of the present disclosure, a tetragonal ruthenium oxide, and a hydrous ruthenium oxide.

FIG. 3 shows TPD-MS (Temperature Programmed Desorption-Mass Spectrometry) data of the monoclinic ruthenium oxide ($H_xRuO_2$) prepared according to an embodiment of the present disclosure.

BEST MODE FOR CARRYING OUT THE INVENTION

Figure 1A:
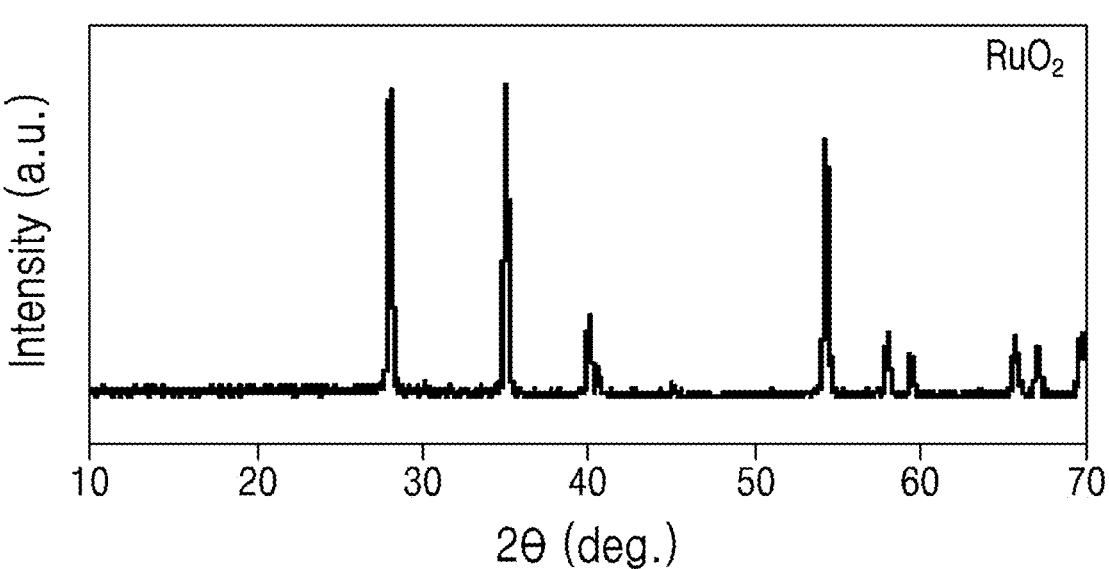

Hereinafter, embodiments and examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through this whole specification, a phrase in the form "A and/or B" means "A or B, or A and B".

Hereinafter, embodiments of the present disclosure have been described in detail, but the present disclosure may not be limited thereto.

A first aspect of the present disclosure provides a ruthenium oxide with a monoclinic structure and represented by the following Chemical Formula I:

$$H_xRuO_2;$$ [Chemical Formula I]

in Chemical Formula I, $0 < x \leq 4$.

In an embodiment of the present disclosure, x (atomic ratio of hydrogen) in Chemical Formula I may be more than 0 to 4 or less, about 0.1 to about 3.5, about 0.1 to about 3, about 0.1 to about 2.5, about 0.1 to about 2, about 0.1 to about 1.5, about 0.1 to about 1.2, about 0.2 to about 3.5, about 0.2 to about 3, about 0.2 to about 2.5, about 0.2 to about 2, about 0.2 to about 1.5, about 0.2 to about 1.2, about 0.3 to about 3.5, about 0.3 to about 3, about 0.3 to about 2.5, about 0.3 to about 2, about 0.3 to about 1.5, about 0.3 to about 1.2, about 0.4 to about 3.5, about 0.4 to about 3, about 0.4 to about 2.5, about 0.4 to about 2, about 0.4 to about 1.5, or about 0.4 to about 1.2, but is not limited thereto.

In an embodiment of the present disclosure, as x (atomic ratio of hydrogen) in Chemical Formula I is closer to about 0.8, it may be easier to produce the monoclinic ruthenium oxide. Specifically, when the atomic ratio of hydrogen is from about 0.4 to about 1.2, it may be easier to produce the monoclinic ruthenium oxide. Here, when x in Chemical Formula I is 0, a structural transition to a tetragonal rutile structure may occur in the ruthenium oxide. Therefore, it is desirable to maintain the hydrogen content.

In an embodiment of the present disclosure, the atomic ratio of hydrogen in Chemical Formula I may be calculated by thermo-gravimetric analysis (TGA). Specifically, in the thermo-gravimetric analysis, a solid sample is placed in a platinum container and then weight changes are measured while raising the temperature. All of the hydrogen contained in the monoclinic ruthenium oxide ($H_xRuO_2$) is removed, and the monoclinic ruthenium oxide ($H_xRuO_2$) is converted into a tetragonal ruthenium oxide ($RuO_2$). The amount of hydrogen can be quantitatively analyzed from the weight changes with temperature.

In an embodiment of the present disclosure, the ruthenium oxide may include more than 0 parts by weight to about 3 parts by weight or less of hydrogen based on 100 parts by weight of the ruthenium oxide, but is not limited thereto. For example, when Chemical Formula I is $H_4RuO_2$, the ruthenium oxide may include 3.01 parts by weight of H(hydrogen) based on 100 parts by weight of $RuO_2$, but is not limited thereto. In an embodiment of the present disclosure, even if hydrogen is somewhat excessive or deficient in terms of stoichiometric ratio, it does not significantly affect the monoclinic structure, but in the presence of hydrogen, it is easy to produce a monoclinic ruthenium oxide. The product is stable in a reducing atmosphere and thus can be easily used as a hydrogenation catalyst and can also be reused. In an embodiment of the present disclosure, the ruthenium oxide may include more than 0 parts by weight to about 3 parts by weight or less, more than 0 parts by weight to about 2.5 parts by weight or less, more than 0 parts by weight to about 2 parts by weight or less, more than 0 parts by weight to about 1.5 parts by weight or less, more than 0 parts by weight to about 1 parts by weight or less, or more than 0 parts by weight to about 0.5 parts by weight or less of hydrogen based on 100 parts by weight of the ruthenium oxide, but is not limited thereto.

In an embodiment of the present disclosure, diffraction peaks of the ruthenium oxide may be observed at respective positions corresponding to incident angles (2θ) of 18.38°<2θ<18.42°, 25.45°<2θ<25.51°, 26.26°<2θ<26.32°, 33.45°<2θ<33.51°, 35.28°<2θ<35.34°, 36.24°<2θ<36.30°, 37.32°<2θ<37.38°, 39.55°<2θ<39.61°, 40.61°<2θ<40.67°, 41.46°<2θ<41.52°, 49.17°<2θ<49.23°, 52.31°<2θ<52.37°, 54.03°<2θ<54.09°, 54.70°<2θ<54.76°, 55.95°<2θ<56.01°, 59.97°<2θ<60.03°, 60.40°<2θ<60.46°, 61.92°<2θ<61.98°, 63.94°<2θ<64.00°, 65.79°<2θ<65.85° and 69.13°<2θ<69.19° as determined by X-ray powder diffraction measurement (Cu Kα rays). In an embodiment of the present disclosure, diffraction peaks of the ruthenium oxide may be observed at respective positions corresponding to incident angles (2θ) of 18.40°, 25.48°, 26.29°, 33.48°, 35.31°, 36.27°, 37.35°, 39.58°, 40.64°, 41.49°, 49.20°, 52.34°, 54.06°, 54.73°, 55.98°, 58.00°, 60.43°, 61.95°, 63.97°, 65.82° and 69.16° as determined by X-ray powder diffraction measurement (Cu Kα rays).

In an embodiment of the present disclosure, the ruthenium oxide may have a structure of a monoclinic space group $P2_1/c$, $C2/m$, $P2/c$, $C2/c$, $P2_1/m$ or $P2_1/m$, but is not limited thereto.

Figure 5:
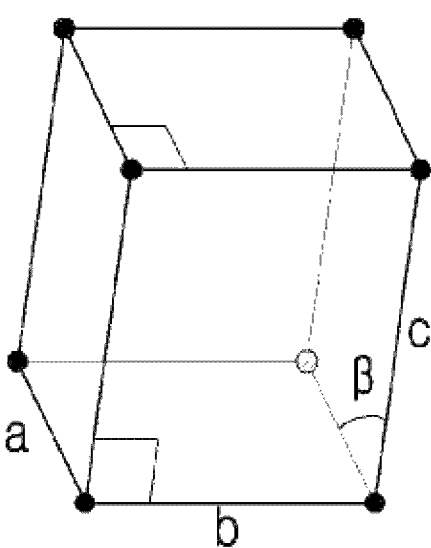
FIG. 5 shows a unit cell of the monoclinic crystal structure of the ruthenium oxide where lattice constants a to c and an angle between the edges are defined therein.

In an embodiment of the present disclosure, a unit cell of the monoclinic crystal structure of the ruthenium oxide may be represented as shown in FIG. 5, and lattice constants a to c and an angle between the edges may be defined as shown in FIG.

In an embodiment of the present disclosure, the monoclinic structure may have lattice constants of 5 Å≤a≤6 Å, 5 Å≤b≤6 Å and 5≤c≤6 Å, and a beta (β) angle of about 110° to about 120°. For example, each of the a and the c may be about 5 Å to about 6 Å, about 5.1 Å to about 6 Å, about 5.2 Å to about 6 Å, about 5.3 Å to about 6 Å, about 5 Å to about 5.8 Å, about 5.1 Å to about 5.8 Å, about 5.2 Å to about 5.8 Å, about 5.3 Å to about 5.8 Å, about 5 Å to about 5.6 Å, about 5.1 Å to about 5.6 Å, about 5.2 Å to about 5.6 Å, about 5.3 Å to about 5.6 Å, about 5 Å to about 5.4 Å, about 5.1 Å to about 5.4 Å, about 5.2 Å to about 5.4 Å, about 5.3 Å to about 5.4 Å, or about 5.35 Å to about 5.4 Å, the b may be about 5 Å to about 6 Å, about 5 Å to about 5.8 Å, about 5 Å to about 5.6 Å, about 5 Å to about 5.4 Å, about 5 Å to about 5.2 Å, or about 5 Å to about 5.1 Å, and the beta (β) angle may be about 110° to about 120°, about 112° to about 120°, about 114° to about 120°, about 110° to about 118°, about 112° to about 118°, about 114° to about 118°, about 110° to about 116°, about 112° to about 116°, or about 114° to about 116°.

In an embodiment of the present disclosure, the monoclinic structure may have lattice constants of a=5.3533 Å, b=5.0770 Å, and c=5.3532 Å, and a beta (β) angle of 115.9074°, but is not limited thereto.

A second aspect of the present disclosure provides a method of preparing a ruthenium oxide, including: hydrothermally treating a tetragonal ruthenium oxide in the presence of at least one of carbon monoxide and carbon dioxide, and water in a pressure reactor to obtain a monoclinic ruthenium oxide.

In an embodiment of the present disclosure, hydrogen may be further included during the hydrothermally treating in the pressure reactor, but the present disclosure is not limited thereto.

In an embodiment of the present disclosure, the tetragonal ruthenium oxide may be hydrothermally treated in the presence of 1) carbon monoxide and water ($CO+H_2O$), 2) carbon dioxide, hydrogen and water ($CO_2+H_2+H_2O$), 3) carbon monoxide, water and hydrogen ($CO+H_2O+H_2$), and 4) carbon monoxide, water, carbon dioxide and hydrogen ($CO+H_2O+CO_2+H_2$) in the pressure reactor.

In an embodiment of the present disclosure, the tetragonal ruthenium oxide may have a purity of about 3N (99.9 mass %) or more. If the purity of the tetragonal ruthenium oxide is less than about 3N, the yield of the reactant may be lowered, or ruthenium metal may be generated.

In an embodiment of the present disclosure, a weight ratio of the ruthenium oxide to the water may be more than about 2:1 to less than about 1:10, but is not limited thereto. If the weight ratio of the ruthenium oxide to the water is about 1:10 or more, the production of the monoclinic ruthenium oxide may be delayed, and if the weight ratio of the ruthenium oxide to the water is about 2:1 or less, the reaction may not proceed and the tetragonal ruthenium oxide may remain without being reacted.

In an embodiment of the present disclosure, a pressure range of the carbon monoxide may be about 1 MPa to about 5 MPa, but is not limited thereto. For example, the pressure range of the carbon monoxide may be about 1 MPa to about 5 MPa, about 1 MPa to about 4 MPa, about 1 MPa to about 3 MPa, or 1 MPa to about 2 MPa, but is not limited thereto. If the pressure range of the carbon monoxide is less than about 1 MPa, the production of the monoclinic ruthenium oxide may be delayed, and if the pressure range of the carbon monoxide is about 5 MPa or more, impurities such as ruthenium metal or ruthenium carbonyl may be generated. In an embodiment of the present disclosure, the pressure range of the carbon monoxide is most preferably about 1 MPa to about 1.5 MPa.

In an embodiment of the present disclosure, the pressure range of the carbon dioxide is most preferably about 3 MPa to about 12 MPa. For example, the pressure range of the carbon dioxide may be about 3 MPa to about 12 MPa, about 3 MPa to about 10 MPa, about 3 MPa to about 8 MPa, about 3 MPa to about 6 MPa, about 3 MPa to about 4 MPa, about 5 MPa to about 12 MPa, about 5 MPa to about 10 MPa, about 5 MPa to about 8 MPa, about 5 MPa to about 6 MPa, about 7 MPa to about 12 MPa, about 7 MPa to about 10 MPa, or about 7 MPa to about 8 MPa, but is not limited thereto.

In an embodiment of the present disclosure, a pressure range of the hydrogen is most preferably about 0.5 MPa to about 1.5 MPa. For example, the pressure range of the hydrogen may be about 0.5 MPa to about 1.3 MPa, about 0.5 MPa to about 1.1 MPa, about 0.5 MPa to about 0.9 MPa, about 0.5 MPa to about 0.7 MPa, about 0.7 MPa to about 1.5 MPa, about 0.7 MPa to about 1.3 MPa, about 0.7 MPa to about 1.1 MPa, or about 0.7 MPa to about 0.9 MPa, but is not limited thereto.

In an embodiment of the present disclosure, a temperature range of the hydrothermally treating may be about 150° C. to about 300° C., but is not limited thereto. For example, the temperature range of the hydrothermally treating may be about 150° C. to about 300° C., about 150° C. to about 280° C., about 150° C. to about 260° C., about 150° C. to about 240° C., about 160° C. to about 300° C., about 160° C. to about 280° C., about 160° C. to about 260° C., or about 160° C. to about 240° C., but is not limited thereto. In an embodiment of the present disclosure, the temperature range of the hydrothermally treating is most preferably about 180° C. to about 220° C.

In an embodiment of the present disclosure, if the temperature range of the hydrothermally treating is less than about 150° C., the reaction may not proceed well, and if the temperature range of the hydrothermally treating is more than about 300° C., the monoclinic ruthenium oxide may be produced well, but the particles may increase in size and impurities such as ruthenium metal may be generated. Also, if the temperature range of the hydrothermally treating is not about 150° C. to about 300° C., a ruthenium oxide having low crystallinity can be generated.

A third aspect of the present disclosure provides a catalyst including the ruthenium oxide according to the first aspect, and the catalyst is used for selective hydrogenation of an aromatic compound or an unsaturated compound.

In an embodiment of the present disclosure, the catalyst may be used in the amount of about 0.01 part by weight to about 10 parts by weight based on 100 parts by weight of the aromatic compound or the unsaturated compound, but is not limited thereto. If the amount of the catalyst is less than about 0.01 part by weight, the hydrogenation time may be increased and the reaction may not be completed, and if it is more than about 10 parts by weight, the hydrogenation may be accelerated, but the selectivity of the product may be lowered due to generation of by-products.

In an embodiment of the present disclosure, the selective hydrogenation may be performed in an autoclave. Herein, the temperature and pressure may vary depending on the type of the reactant.

In an embodiment of the present disclosure, a pressure range of the hydrogen in the hydrogenation may be about 0.1 MPa to about 10 MPa, but is not limited thereto. For example, the pressure range of the hydrogen in the hydrogenation may be about 0.1 MPa to about 10 MPa, about 0.1 MPa to about 8 MPa, about 0.1 MPa to about 6 MPa, about 1 MPa to about 10 MPa, about 1 MPa to about 8 MPa, or about 1 MPa to about 6 MPa, but is not limited thereto. In an embodiment of the present disclosure, the pressure range of the hydrogen in the hydrogenation is most preferably about 2 MPa.

In an embodiment of the present disclosure, a temperature range of the hydrogenation may be about 20° C. to about 200° C., but is not limited thereto. For example, the temperature range of the hydrogenation may be about 20° C. to about 200° C., about 20° C. to about 190° C., about 20° C. to about 180° C., about 20° C. to about 170° C., about 20° C. to about 160° C., about 20° C. to about 150° C., or about 20° C. to about 140° C., but is not limited thereto. In an embodiment of the present disclosure, the temperature range of the hydrogenation may be about 20° C. to about 70° C. or about 120° C. to about 130° C.

In an embodiment of the present disclosure, a reaction time of the hydrogenation may be increased to maximize the yield in the above-described the temperature range and the pressure range conditions.

In an embodiment of the present disclosure, the aromatic compound or the unsaturated compound may be a compound containing at least one selected from an alkenyl group, an alkynyl group, and a phenyl group, but is not limited thereto.

In an embodiment of the present disclosure, the aromatic compound or the unsaturated compound may include at least one selected from benzene, toluene, dibenzyltoluene, xylene, phenol, styrene, and n-ethylcarbazole, but is not limited. In an embodiment of the present disclosure, the aromatic compound or the unsaturated compound may be toluene, dibenzyltoluene, and n-ethylcarbazole.

In an embodiment of the present disclosure, when a solvent is used in the hydrogenation, aliphatic compounds including n-pentane, n-hexane, n-heptane, n-octane, n-nonane, n-decane, etc. and cycloalkane hydrocarbons including cyclohexane, cycloheptane, cyclooctane, cyclononane, cyclodecane, etc. may be used as the solvent for the hydrogenation, but the present disclosure is not limited thereto. In an embodiment of the present disclosure, cyclohexane may be used as the solvent for the hydrogenation.

According to the embodiments of the present disclosure, the monoclinic ruthenium oxide can be used as a catalyst for hydrogenation even at a low temperature.

According to the embodiments of the present disclosure, a hydrogenation catalyst can be reused as long as hydrogen is present in the monoclinic ruthenium oxide with a chemical formula of $H_xRuO_2$.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

Example 1

A ruthenium oxide ($RuO_2$) was purchased from Sigma-Aldrich (St. Louis, USA). The purchased ruthenium oxide was used, and the ruthenium oxide ($RuO_2$) was found to have a tetragonal rutile structure through X-ray diffraction.

After 0.3 g of the ruthenium oxide was put into an autoclave together with 1.0 mL of distilled water, the lid was closed. After the oxygen content in the autoclave was reduced by injecting carbon monoxide three times into the autoclave, the autoclave was filled to a carbon monoxide pressure of 1.0 MPa to 1.5 MPa. When the internal temperature of the autoclave reached 180° C. to 220° C., the temperature increase was terminated and the reaction was carried out at the above-described temperature for 5 hours to 12 hours. After the reaction, the product was vacuum dried. The crystal phase of the dried product was analyzed by X-ray diffraction, and as a result of the analysis, the crystal structure of the product was found to correspond to a monoclinic ruthenium oxide, and a peak corresponding to the tetragonal ruthenium oxide used as the reactant was not observed. The amount of the obtained monoclinic ruthenium oxide was 0.287 g, and the yield of the monoclinic ruthenium oxide was 95.67% based on the tetragonal ruthenium oxide used as the reactant.

Figure 1B:
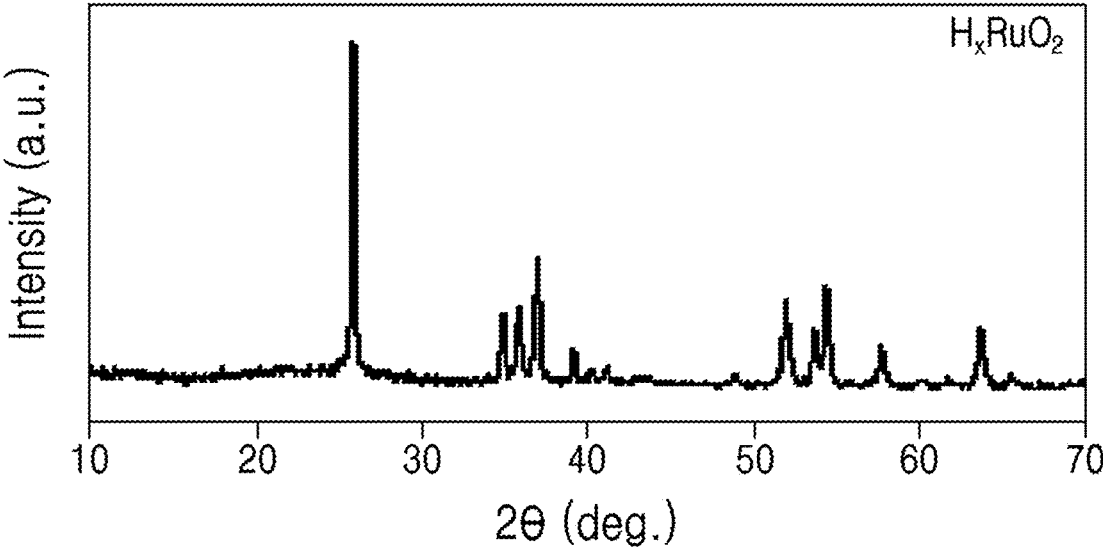

FIG. 1B shows X-ray powder diffraction data of the monoclinic ruthenium oxide ($H_xRuO_2$) prepared according to Example 1. Diffraction peaks of the ruthenium oxide are observed at respective positions corresponding to incidence angles ($2\theta$) of 18.40°, 25.48°, 26.29°, 33.48°, 35.31°, 36.27°, 37.35°, 39.58°, 40.64°, 41.49°, 49.20°, 52.34°, 54.06°, 54.73°, 55.98°, 58.00°, 60.43°, 61.95°, 63.97°, 65.82° and 69.16° by X-ray powder diffraction measurement (Cu Kα rays).

Figure 1C:
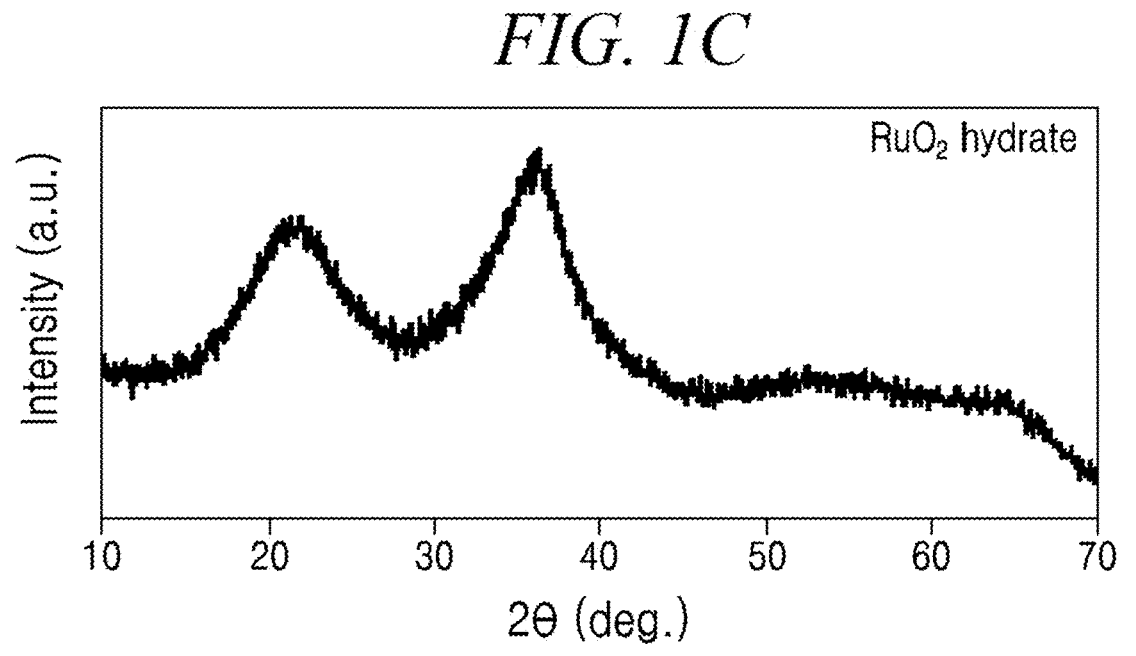

As shown in FIG. 1A to FIG. 1C, the monoclinic ruthenium oxide ($H_xRuO_2$) exhibits a characteristic X-ray powder diffraction peak different from that of the tetragonal rutile ruthenium oxide.

Figure 2:
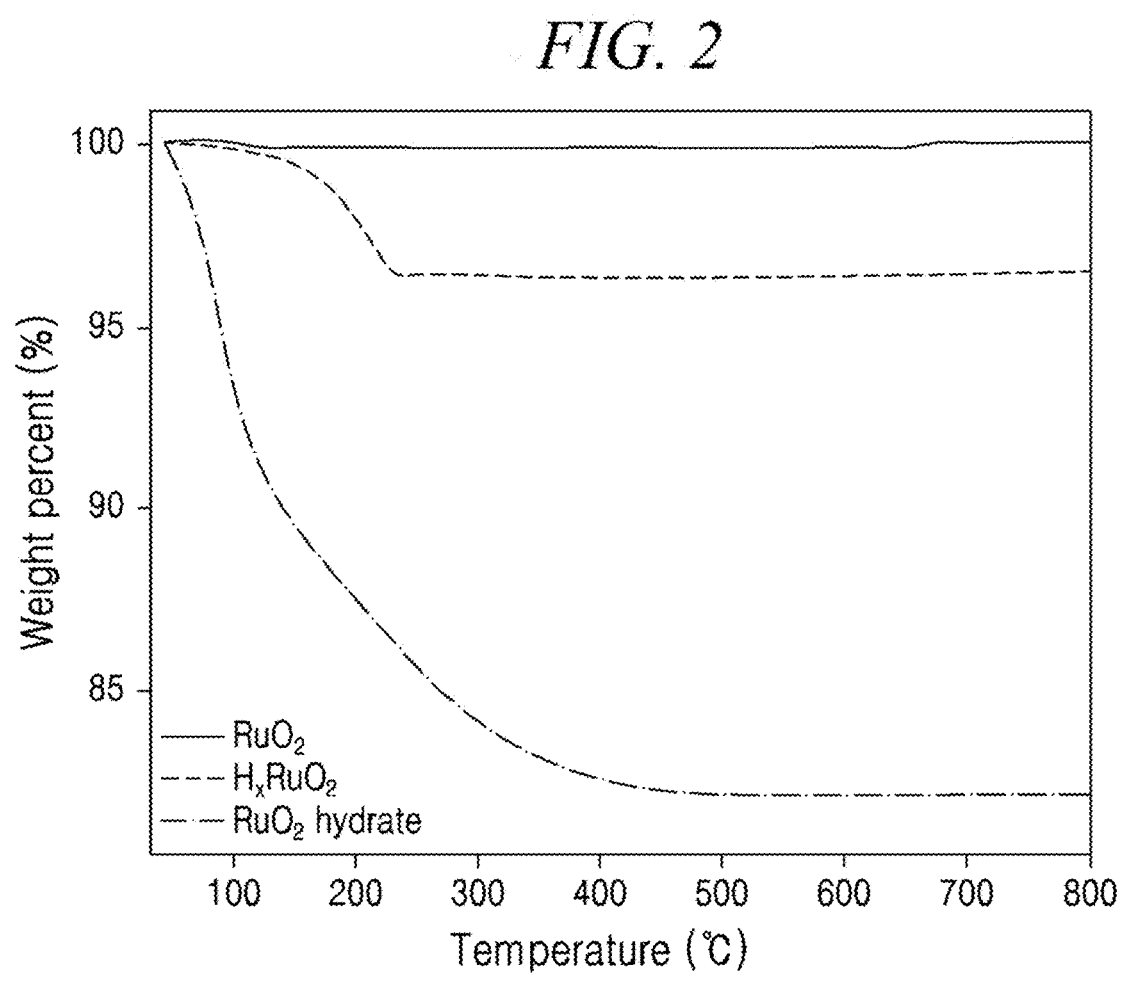

FIG. 2 is a thermo-gravimetric analysis (TGA) graph of the monoclinic ruthenium oxide ($H_xRuO_2$) prepared according to Example 1. After the thermo-gravimetric analysis, it was found from the X-ray powder diffraction data that all of the monoclinic ruthenium oxide, the tetragonal ruthenium oxide and the hydrous ruthenium oxide were converted into a tetragonal ruthenium oxide.

Specifically, in the thermo-gravimetric analysis, a solid sample is placed in a platinum container and then weight changes are measured while raising the temperature, and all of the hydrogen contained in the prepared monoclinic ruthenium oxide ($H_xRuO_2$) is blown away, and the monoclinic ruthenium oxide ($H_xRuO_2$) is converted into a tetragonal ruthenium oxide. Through the thermo-gravimetric analysis, the amount of hydrogen was quantitatively analyzed from the weight changes with temperature.

Figure 3:
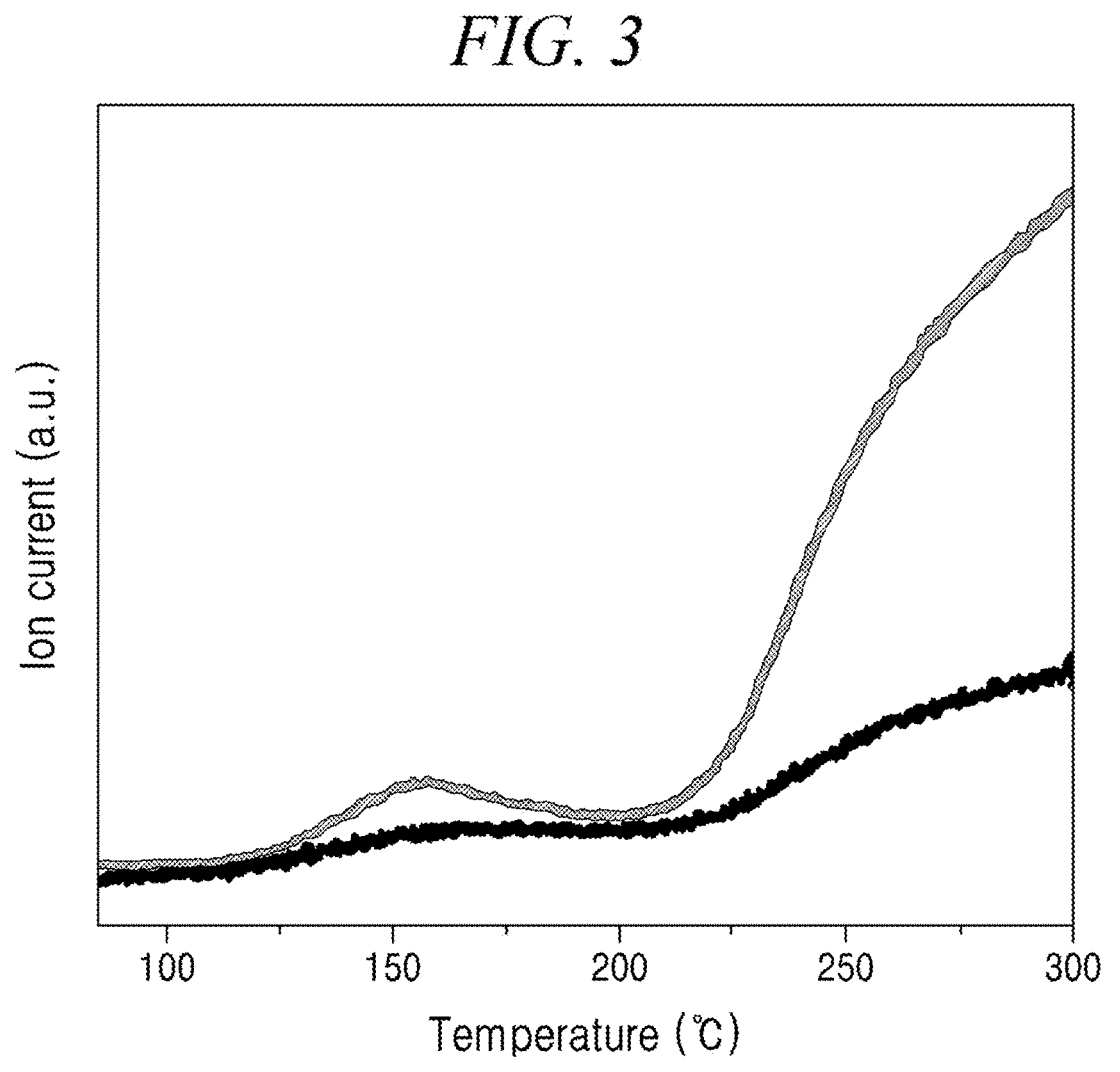

FIG. 3 shows TPD-MS (Temperature Programmed Desorption-Mass Spectrometry) data of the monoclinic ruthenium oxide ($H_xRuO_2$) prepared according to Example 1. It can be seen that as the reaction temperature increases, hydrogen (hydrogen molecules with m/z=2, black) and water (water molecules with m/z=18, gray) are released together.

Figure 4:
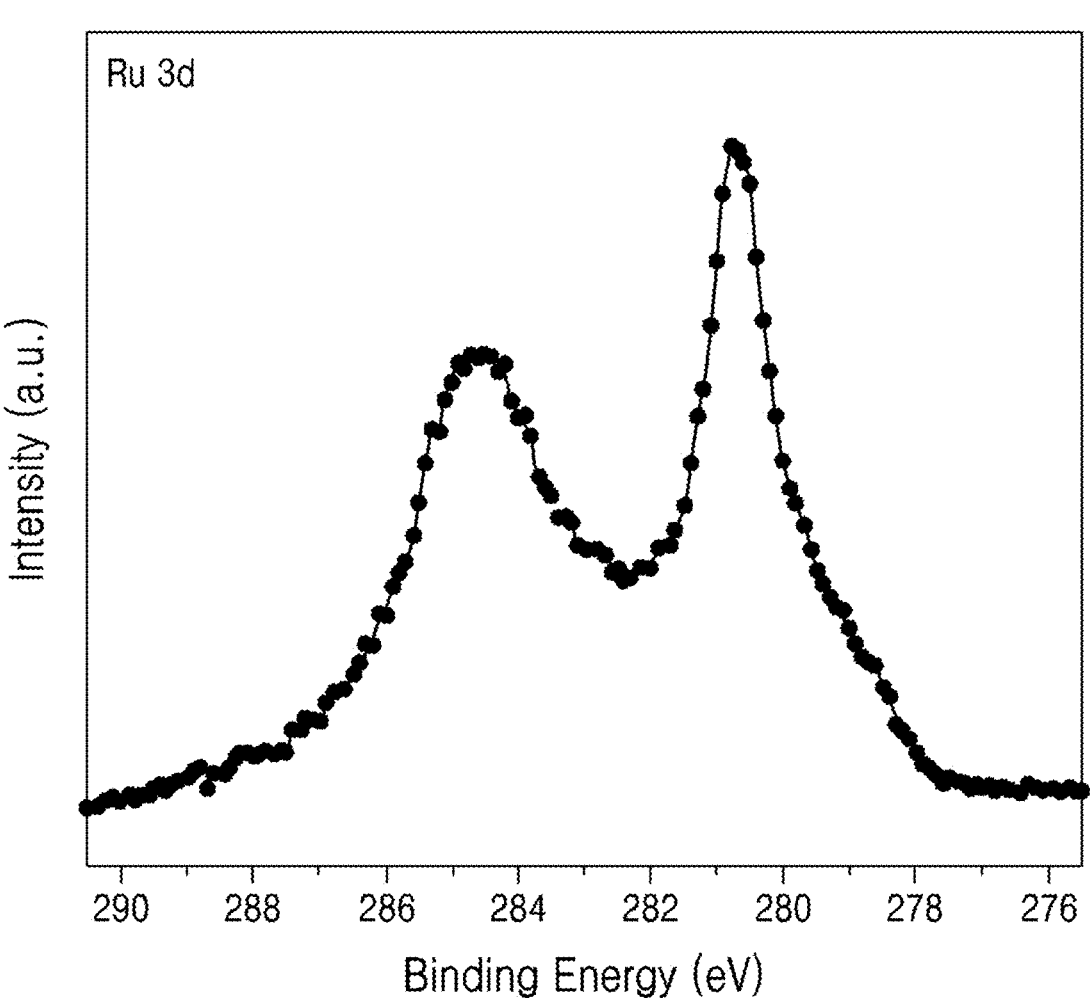
FIG. 4 shows X-ray photoelectron spectroscopy (XPS) data of a monoclinic ruthenium oxide ($H_xRuO_2$) prepared according to Example 1.

FIG. 4 shows X-ray photoelectron spectroscopy (XPS) data of the monoclinic ruthenium oxide ($H_xRuO_2$) prepared according to Example 1.

Comparative Example 1

A hydrothermal synthesis was performed in the same manner as in Example 1 except that carbon monoxide was not added. The crystal phase of the dried product was analyzed by X-ray diffraction, and as a result of the analysis, almost all of the tetragonal ruthenium oxide used as the reactant remained and any peak corresponding to the monoclinic ruthenium oxide was not observed.

Comparative Example 2

A synthesis was performed in the same manner as in Example 1 except that water was not added. The crystal phase of the dried product was analyzed by X-ray diffraction, and as a result of the analysis, the tetragonal ruthenium oxide used as the reactant remained and a very small amount of the tetragonal ruthenium oxide was converted into a monoclinic ruthenium oxide.

Example 2

A monoclinic ruthenium oxide was synthesized in an autoclave with 1.0 mL of distilled water in the same manner as in Example 1 except that carbon dioxide and hydrogen were used instead of carbon monoxide. After the oxygen content and the water content in the autoclave were reduced by injecting carbon dioxide three times into the autoclave, the autoclave was filled to a carbon dioxide pressure of from 1.0 MPa to 3.0 MPa and a hydrogen pressure of from 0.5 MPa to 1.5 MPa. When the internal temperature of the autoclave reached 180° C. to 220° C., the temperature increase was terminated and the reaction was carried out at the above-described temperature for 5 hours to 12 hours. After the reaction, the product was vacuum dried. The crystal phase of the dried product was analyzed by X-ray diffraction, and as a result of the analysis, ruthenium metal was produced as impurities together with a monoclinic ruthenium oxide. The amount of the obtained monoclinic ruthenium oxide was 0.226 g, and the yield ratio of the monoclinic ruthenium oxide was 75.33% based on the tetragonal ruthenium oxide used as the reactant.

Example 3

A reaction was carried out in the same manner as in Example 1 except that hydrogen was additionally injected. The crystal phase of the dried product was analyzed by X-ray diffraction, and it was confirmed that polyethylene was produced as impurities together with a monoclinic ruthenium oxide according to the analysis result. The amount of the obtained monoclinic ruthenium oxide was 0.131 g, and the yield ratio of the monoclinic ruthenium oxide was 43.67% based on the tetragonal ruthenium oxide used as the reactant.

Example 4

A reaction was carried out in the same manner as in Example 1 except that carbon dioxide and hydrogen were additionally injected. The crystal phase of the dried product was analyzed by X-ray diffraction, and it was confirmed that impurities were produced together with a monoclinic ruthenium oxide according to the analysis result. The amount of the obtained monoclinic ruthenium oxide was 0.164 g, and the yield ratio of the monoclinic ruthenium oxide was 54.67% based on the tetragonal ruthenium oxide used as the reactant.

1) Test Example

Test Example 1 (Using Toluene)

Toluene was hydrogenated using the monoclinic ruthenium oxide ($H_xRuO_2$) prepared in each of Examples 1 and 2 and Comparative Examples 1 and 2 as a catalyst. A 10 mL Pyrex glass container was placed inside an autoclave, and 10 mg of the monoclinic ruthenium oxide and 1 mL of toluene were put thereinto together with a magnetic bar. After hydrogen was blown into the autoclave to remove other gases therein, the autoclave was filled to a hydrogen pressure of 2.0 MPa. Then, the internal temperature of the autoclave was adjusted to 20° C. to 70° C. with stirring at 300 rpm. When the internal temperature of the autoclave reached a reaction temperature, the temperature increase was terminated, and hydrogenation was carried out. One hour after starting the reaction, the autoclave was cooled by using an ice bath and the product inside was obtained. The degree of hydrogenation was analyzed by NMR spectroscopy.

Test Example 2 (Using n-ethyl Carbazole)

N-ethylcarbazole was hydrogenated in the same manner as in Test Example 1 except that n-ethylcarbazole was used as a hydrogenation material instead of toluene. A magnetic bar together with 10 mg of the monoclinic ruthenium oxide and 0.1 g of NEC were put into a Pyrex glass container placed inside an autoclave. After the autoclave was filled to a hydrogen pressure of 5.0 MPa, the internal temperature of the autoclave was adjusted to 120° C. to 130° C. When the internal temperature of the autoclave reached a reaction temperature, the temperature increase was terminated, and hydrogenation was carried out. Three hours after starting the reaction, the autoclave was cooled by using an ice bath and the product inside was analyzed by NMR spectroscopy.

Test Example 3 (Using Dibenzyltoluene)

Dibenzyltoluene was hydrogenated in the same manner as in Test Example 2 except that dibenzyltoluene was used as a hydrogenation material instead of n-ethylcarbazole. A magnetic bar together with 10 mg of the monoclinic ruthenium oxide and 0.2 mL of dibenzyltoluene were put into a Pyrex glass container placed inside an autoclave. After the autoclave was filled to a hydrogen pressure of 5.0 MPa, the internal temperature of the autoclave was adjusted to 120° C. to 130° C. When the internal temperature of the autoclave reached a reaction temperature, the temperature increase was terminated, and hydrogenation was carried out. Three hours after starting the reaction, the autoclave was cooled by using an ice bath and the product inside was analyzed by NMR spectroscopy.

2) Hydrogenation Test Result

TABLE 1

| Entry | Catalyst | solvent | T[° C.] | P(H₂)[MPa] | t[h] | Conversion[%] |
|---|---|---|---|---|---|---|
| 1 | RuO₂ | — | 70 | 2 | 1 | 16.67 |
| 2 | RuO₂ | Cyclohexane | 70 | 2 | 1 | 20.63 |
| 3 | 5% Ru@Al₂O₃ | — | 70 | 2 | 1 | 23.66 |
| 4 | 5% Ru@Al₂O₃ | Cyclohexane | 70 | 2 | 1 | 13.04 |
| 5 | HₓRuO₂ | — | 70 | 2 | 1 | 100 |
| 6 | HₓRuO₂ | Cyclohexane | 70 | 2 | 1 | 100 |

Table 1 shows the catalytic activity for conversion into methylcyclohexane through hydrogenation using toluene (Test Example 1), and the catalysts used herein are a monoclinic ruthenium oxide ($H_xRuO_2$) and a tetragonal ruthenium oxide ($RuO_2$) as well as a commercial catalyst, i.e., 5 wt % Ru/Al₂O₃. Cyclohexane was used as a solvent, and the reaction was also carried out without a solvent. Catalyst (g): Toluene (mL)=1:100.

TABLE 2

| Entry | Catalyst | Reactant | T[° C.] | P(H₂)[MPa] | t[h] | Conversion[%] |
|---|---|---|---|---|---|---|
| 1 | RuO₂ | Dibenzyltoluene | 120 | 5 | 3 | 41.2 |
| 2 | HₓRuO₂ | Dibenzyltoluene | 120 | 5 | 3 | 100 |
| 3 | RuO₂ | N-ethylcarbazole | 120 | 5 | 3 | 33.4 |
| 4 | HₓRuO₂ | N-ethylcarbazole | 120 | 5 | 3 | 100 |

Table 2 shows the catalytic activity for conversion through hydrogenation using n-ethylcarbazole (Test Example 2) and dibenzyltoluene (Test Example 3), and the catalysts used herein are a monoclinic ruthenium oxide ($H_xRuO_2$) and a tetragonal ruthenium oxide ($RuO_2$), and the reaction was carried out without a solvent. Catalyst (g): n-ethylcarbazole (g)=1:10. Catalyst (g): dibenzyltoluene (mL)=1:20.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A ruthenium oxide with a monoclinic structure and represented by the following Chemical Formula I:

$$H_xRuO_2;$$ [Chemical Formula I]

in Chemical Formula I, 0<x≤4.

2. The ruthenium oxide of claim 1, wherein the ruthenium oxide includes more than 0 parts by weight to 3 parts by weight or less of hydrogen based on 100 parts by weight of the ruthenium oxide.

3. The ruthenium oxide of claim 1, wherein diffraction peaks of the ruthenium oxide is observed at respective positions corresponding to incident angles (2θ) of 18.38°<2θ<18.42°, 25.45°<2θ<25.51°, 26.26°<2θ<26.32°, 33.45°<2θ<33.51°, 35.28°<2θ<35.34°, 36.24°<2θ<36.30°, 37.32°<2θ<37.38°, 39.55°<2θ<39.61°, 40.61°<2θ<40.67°, 41.46°<2θ<41.52°, 49.17°<2θ<49.23°, 52.31°<2θ<52.37°, 54.03°<2θ<54.09°, 54.70°<2θ<54.76°, 55.95°<2θ<56.01°, 59.97°<2θ<60.03°, 60.40°<2θ<60.46°, 61.92°<2θ<61.98°, 63.94°<2θ<64.00°, 65.79°<2θ<65.85°, and 69.13°<2θ<69.19° as determined by X-ray powder diffraction measurement (Cu Kα rays).

4. The ruthenium oxide of claim 1, wherein the ruthenium oxide has a structure of a monoclinic space group P2₁/c, C2/m, P2/c, C2/c, P2/m or P2₁/m.

5. The ruthenium oxide of claim 1, wherein the monoclinic structure has lattice constants of 5 Å≤a≤6 Å, 5 Å≤b≤6 Å and 5 Å≤c≤6 Å, and a beta (β) angle of 110° to 120°.

6. The ruthenium oxide of claim 1, wherein the monoclinic structure has lattice constants of a=5.3533 Å, b=5.0770 Å and c=5.3532 Å, and a beta (β) angle of 115.9074°.

7. A catalyst comprising the ruthenium oxide according to claim 1, wherein the catalyst is used for selective hydrogenation of an aromatic compound or an unsaturated compound.

8. The catalyst of claim 7, wherein the catalyst is used in the amount of 0.01 part by weight to 10 parts by weight based on 100 parts by weight of the aromatic compound or the unsaturated compound.

9. The catalyst of claim 7,
wherein a pressure range of the hydrogen in the hydrogenation is 0.1 MPa to 10 MPa.

10. The catalyst of claim 7,
wherein a temperature range of the hydrogenation is 20° C. to 200° C.

11. The catalyst of claim 7,
wherein the aromatic compound or the unsaturated compound is a compound containing at least one selected from an alkenyl group, an alkynyl group, and a phenyl group.

12. The catalyst of claim 11,
wherein the aromatic compound or the unsaturated compound includes at least one selected from benzene, toluene, dibenzyltoluene, xylene, phenol, styrene, and n-ethylcarbazole.

* * * * *